US005747467A

United States Patent [19]
Agouridas et al.

[11] Patent Number: 5,747,467
[45] Date of Patent: May 5, 1998

[54] ERYTHROMYCINS

[75] Inventors: Constantin Agouridas, Nogent sur Marne; François Bretin, Ozoir la Ferriere; Jean-François Chantot, Nogent sur Marne, all of France

[73] Assignee: Roussel Uclaf, France

[21] Appl. No.: 767,954

[22] Filed: Dec. 19, 1996

[30] Foreign Application Priority Data

Dec. 22, 1995 [FR] France ...................... 95-15322

[51] Int. Cl.$^6$ ........................... A61K 31/70; C07H 17/08
[52] U.S. Cl. ........................ 514/29; 536/7.2; 536/7.3; 536/7.4
[58] Field of Search .................... 536/7.2, 7.3, 7.4; 514/29

[56] References Cited

U.S. PATENT DOCUMENTS

| | | | |
|---|---|---|---|
| 5,444,051 | 8/1995 | Agouridas et al. | 514/29 |
| 5,527,780 | 6/1996 | Agouridas et al. | 514/29 |

FOREIGN PATENT DOCUMENTS

| | | | |
|---|---|---|---|
| 0487411 | 11/1991 | European Pat. Off. | C07H 17/08 |
| 0596802 | 11/1993 | European Pat. Off. | C07H 17/00 |
| 0676609 | 4/1995 | European Pat. Off. | C07H 17/08 |
| 0680967 | 5/1995 | European Pat. Off. | C07H 17/08 |
| 0487411 | 5/1992 | France . | |
| 0596802 | 5/1994 | France . | |
| 0676409 | 10/1995 | France . | |
| 0680967 | 11/1995 | France . | |
| 2288174 | 10/1995 | United Kingdom | C07D 498/00 |
| 9529929 | 11/1995 | WIPO | C07H 17/08 |

Primary Examiner—Mukund J. Shah
Assistant Examiner—Sabiha N. Qazi
Attorney, Agent, or Firm—Bierman, Muserlian & Lucas

[57] ABSTRACT

A compound selected from the group consisting of a compound of the formula

I wherein X is selected from the group consisting of —(NH)$_a$—, —CH$_2$—, —SO$_2$— and —O—, a is 0 or 1, Y is —(CH$_2$)$_m$- (CH=CH)$_n$ —(CH$_2$)$_o$-, m+n+o≦8, n=o or 1, Ar is aryl optionally substituted with at least one member of the group consisting of —OH, halogen, —NO$_2$, —CN, $$-\overset{O}{\underset{\|}{C}}-R_3, \quad -N\overset{R_a}{\underset{R_b}{\diagdown}}$$

and alkyl, alkenyl, alkynyl, alkoxy, alkenyloxy, alkynyloxy, alkylthio, alkenylthio, alkynylthio, -N-alkyl, -N-alkenyl and N-alkynyl of up to 12 carbon atoms, R$_a$ and R$_b$ individually are hydrogen or alkyl of up to 12 carbon atoms, R$_3$ is selected from the group consisting of alkyl of 1 to 12 carbon atoms, aryl, heteroaryl, carbocyclic aryl, aryloxy, arylthio and heterocyclic aryl, heterocyclic aryloxy and heterocyclic arylthio of 5 to 6 ring members containing at least one heteroatom, Hal is halogen, Z is hydrogen or acyl of an organic carboxylic acid and their non-toxic, pharmaceutically acceptable addition salts having antibacterial properties.

17 Claims, No Drawings

ERYTHROMYCINS

OBJECTS OF THE INVENTION

It is an object of the invention to provide the erythromycins of formula I and their pharmaceutically acceptable acid addition salts and a process for their preparation.

It is another object of the invention to provide novel antibacterial compositions and a method of treating bacterial infections in warm-blooded animals.

These and other objects and advantages of the invention will become obvious from the following detailed description.

THE INVENTION

The novel compositions of the invention are compounds of the formula

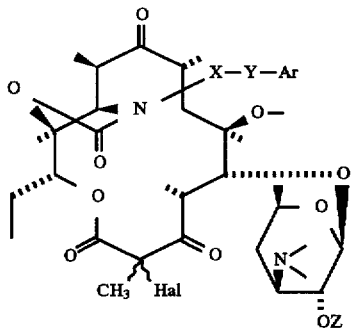

wherein X is selected from the group consisting of —(NH)$_a$—, —CH$_2$—, —SO$_2$— and —O—, a is 0 or 1, Y is —(CH$_2$)$_m$- (CH=CH)$_n$ —(CH$_2$)$_o$-, m+n+o≦8, n=o or 1, Ar is aryl optionally substituted with at least one member of the group consisting of —OH, halogen, —NO$_2$, —CN,

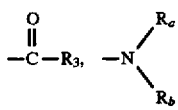

and
alkyl, alkenyl, alkynyl, alkoxy, alkenyloxy, alkynyloxy, alkylthio, alkenylthio, alkynylthio, -N-alkyl, -N-alkenyl and N-alkynyl of up to 12 carbon atoms, R$_a$ and R$_b$ individually are hydrogen or alkyl of up to 12 carbon atoms, R$_3$ is selected from the group consisting of alkyl of 1 to 12 carbon atoms, aryl, heteroaryl, carbocyclic aryl, aryloxy, arylthio and heterocyclic aryl, heterocyclic aryloxy and heterocyclic arylthio of 5 to 6 ring members containing at least one heteroatom, Hal is halogen, Z is hydrogen or acyl of an organic carboxylic acid and their non-toxic, pharmaceutically addition salts.

Examples of aryl of Ar are substituted or unsubstituted phenyl, naphthyl, heterocyclic such as thienyl, furyl, pyrrolyl, thiazolyl, oxazolyl, imidazolyl, thiadiazolyl, pyrazolyl or isopyrazolyl, pyridyl, pyrimidyl, pyridazinyl or pyrazinyl indolyl, benzofuranyl, benzothiazyl and quinolinyl.

These aryls can contain one or more substituents selected from the group consisting of hydroxyl, halogen, —NO$_2$, —CN, alkyl, alkenyl or alkynyl, O-alkyl, O-alkenyl or O-alkynyl, S-alkyl, S-alkenyl or S-alkynyl and N-alkyl, N-alkenyl or N-alkynyl of up to 12 carbon atoms optionally substituted by one or more halogen atoms,

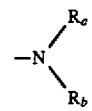

R$_a$ and R$_b$ are individually hydrogen or alkyl of up to 12 carbon atoms and

R$_3$ is alkyl of up to 12 carbon atoms, or an optionally substituted aryl or heteroaryl, carboxylic aryl, O-aryl or S-aryl, or heterocyclic aryl, O-aryl or S-aryl with 5 or 6 ring members containing one or more heteroatoms, optionally substituted by one or more of the substituents mentioned below.

As preferred heterocyclics are

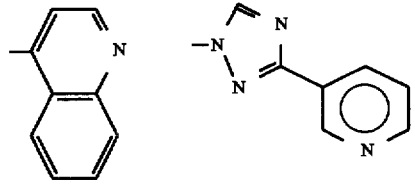

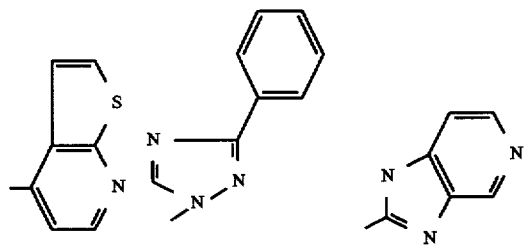

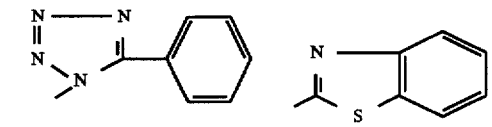

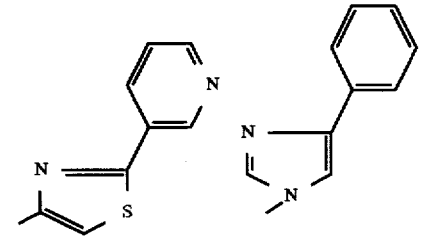

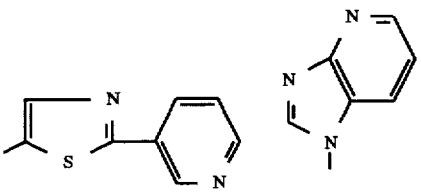

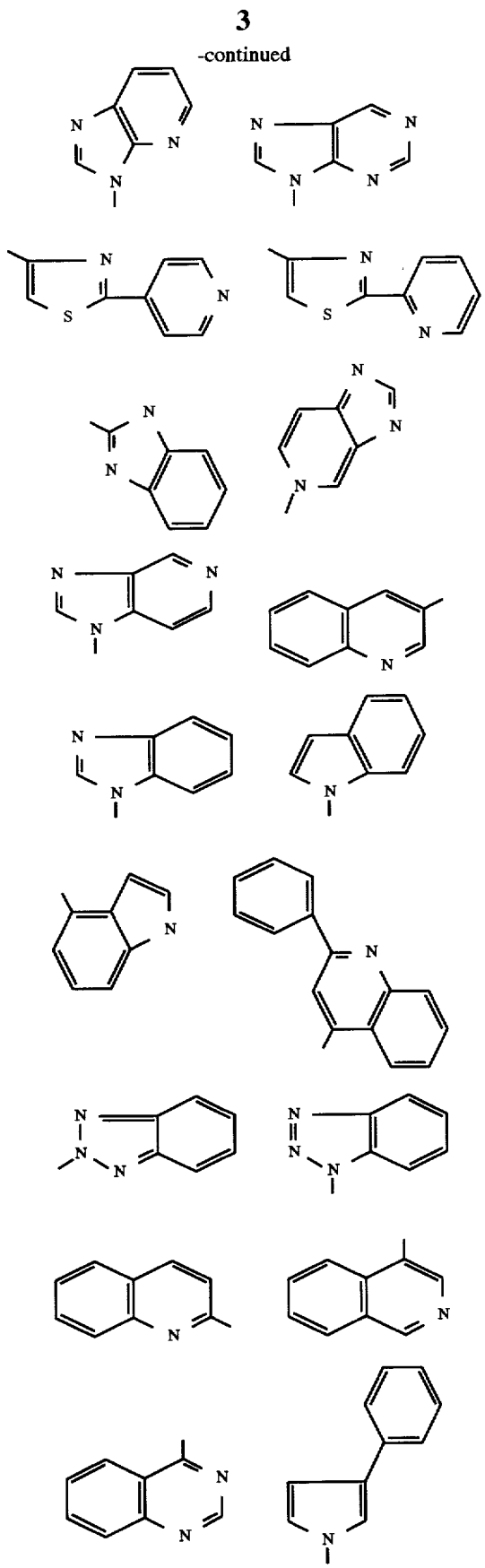
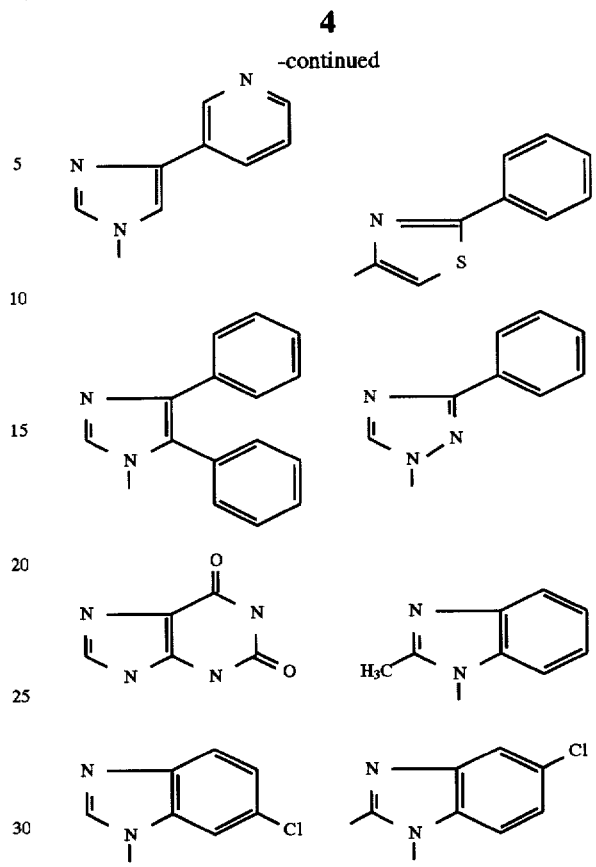

and the heterocyclic radicals envisaged in European Patent Applications No. 487,411, No. 596,802, Nos. 676,409 and No. 680,967. These preferred heterocyclic radicals can be substituted by one or more functional groups. Hal preferably is fluorine, chlorine or bromine.

Examples of acids for the formation of the addition salts are acetic acid, propionic acid, trifluoroacetic acid, malic acid, tartaric acid, methane-sulfonic acid, benzenesulfonic acid, p-toluenesulfonic acid, and in particular stearic acid, ethylsuccinic acid or laurylsulfonic acid.

Among the preferred compounds of formula I are those wherein Z is hydrogen, those wherein X is —(NH)$_a$— where a is 0 or 1, those wherein Hal is fluorine and those wherein Y is —(CH$_2$)$_3$—, —(CH$_2$)$_4$— or —(CH$_2$)$_5$—.

The aryl is preferably aryl heterocyclic wherein Ar is

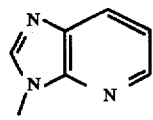

or a 4-quinolinyl optionally mono- or poly-substituted on one and/or the other of the 2 quinoline rings and more preferably Ar is non-substituted 4-quinolinyl. A specific preferred compound of the invention is 11,12-dideoxy-3-de [(2,6-dideoxy-3-C-methyl-3-O-methyl-α-L-ribohexopyranosyl)-oxy]-2-fluoro-6-O-methyl-3-oxo-12,11-(oxycarbonyl( (4-(3H-imidazo(4,5-b)-pyridin-3-yl)-butyl)-imino))-erythromycin A.

The novel bactericidal compositions of the invention are comprised of an antibactericidally effective amount of at least one compound of formula I and their non-toxic, pharmaceutically acceptable acid addition salts and an inert pharmaceutical carrier. The compositions may be in the form of tablets, dragees, capsules, granules, suppositories, ointments, creams, gels or injectable solutions.

Examples of the pharmaceutical carriers are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions possess a very good antibiotic activity on gram ⊕ bacteria such as staphylococci, streptococci and pneumococci and are useful in the treatment of infections caused by sensitive germs and particularly that of staphylococcal infections such as staphylococcal septicemia, malignant staphylococcal infections of the face or skin, pyodermatitis, septic or suppurating sores, boils, anthrax, phlegmons, erysipelas and acne, staphylococcal infections such as primary or post-influenzal acute anginas, bronchopneumonia, pulmonary suppuration, streptococcal infections such as acute anginas, otitis, sinusitis, scarlatina, pneumococcal infections such as pneumonia, bronchitis; brucellosis, diphtheria and gonococcal infection.

The compositions of the invention are also active against infections caused by germs such as Haemophilus influenzae, Rickettsia, Mycoplasma pneumoniae, Chlamydia, Legionella, Ureaplasma, Toxoplasma, or by germs of the Mycobacterium genus.

The novel method of combatting bacterial infections in warm-blooded animals, including humans, comprises administering to warm-blooded animals an antibactericidally effective amount of at least one compound of formula I and their non-toxic, pharmaceutically acceptable acid addition salts. The compounds may be administered orally, rectally, parenterally or topically to the skin or mucous membranes, preferably orally. The usual daily dose is 1.5 to 6 mg/kg depending on the condition treated, the specific compound and the method of administration.

The compositions can also be presented in the form of a powder intended to be dissolved extemporaneously in a suitable vehicle, for example apyrogenic sterile water.

The compounds of formula I may be prepared by reacting a compound of the formula

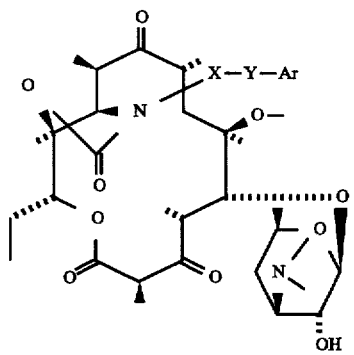

II in which X, Y and Ar are defined as above with a compound of the formula

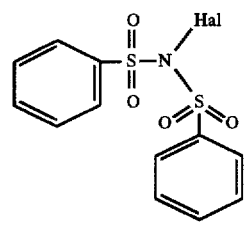

III wherein Hal is defined as above to obtain the corresponding compound of formula I which is optionally subjected to the action of an acid to form the salt. Preferably, the reaction of the compounds of formulae II and III is effected in the presence of a base such as sodium hydride or triethylamine or sodium or potassium carbonate or bicarbonate.

The compounds of formula II used as starting products are described in European Patent Applications No. 487,411, No. 596,802, No. 676,409 and No. 680,967. The products of formula III are commercially available products.

In the following examples, there are described several preferred embodiments to illustrate the invention. However, it is to be understood that the invention is not intended to be limited to the specific embodiments.

EXAMPLE 1

11,12-dideoxy-3-de[(2,6-dideoxy-3-C-methyl-3-0-methyl-α-L-ribohexopyranosyl)-oxy]-2-fluoro-6-0-methyl-3-oxo-12,11-(oxycarbonyl( (4-(3H-imidazo(4,5-b) pyridin-3-yl)-butyl)-imino))-erythromycin (isomer A).

49 mg of sodium hydride were added at 0° C. to a solution of 0.502 g of 11,12-dideoxy-3-de[(2,6-dideoxy-3-C-methyl-3-0-methyl-α-L-ribohexopyranosyl)-oxy]-6-0-methyl-3-oxo-12, 11-oxycarbonyl-[(4-(3H-imidazo(4,5-b)-pyridin-3-yl)-butyl)-imino])-erythromycin A and 5 ml of tetrahydrofuran and the reaction mixture was stirred at 0° C. for one hour. 0.303 g of N-fluoro-N-(phenylsulfonyl) benzene-sulfonamide were added while allowing the temperature to rise. The reaction mixture was stirred for 5 hours, and then was poured into a water+ice mixture. The aqueous phase was extracted using methylene chloride and washed with methylene chloride. The organic phases were combined, dried over magnesium sulfate, filtered and evaporated to dryness to obtain a product which was chromatographed, eluting with a methylene chloride-methanol-ammonium hydroxide mixture (95-5-0.4) to obtain 131.3 mg of the desired product melting at 104°–106° C.

Analyses

|  | C % | H % | F % | N % |
| --- | --- | --- | --- | --- |
| Calculated | 61.2 | 7.8 | 2.4 | 8.7 |
| Found | 61.4 | 8 | 2.2 | 8.4 |

EXAMPLE 2

11,12-dideoxy-3-de[(2,6-dideoxy-3-C-methyl-3-0-methyl-α-L-ribohexopyranosyl)-oxy]-2-fluoro-6-0-methyl-3-oxo-12, 11-(oxycarbonyl-(2-(3-(4-quinolinyl)-2-propyl)-hydrazono))-erythromycin A Using the procedure of Example 1, 11,12-dideoxy-3-de[(2,6-dideoxy-3-C-methyl-3-0-methyl-α-L-ribohexopyranosyl)-oxy]-6-0-methyl-3-oxo-12, 11-(oxycarbonyl-(2-(3-(4-quinolinyl)-2-propyl)-hydrazono))-erythromycin was reacted to obtain the desired product.

EXAMPLE 3

11,12-dideoxy-3-de[(2,6-dideoxy-3-C-methyl-3-0-methyl-α-L-ribohexopyranosyl)-oxy]-2-fluoro-6-0-methyl-3- oxo-12, 11-(oxycarbonyl-((4-(4-(3-pyridinyl)-1H-imidazol-1-yl)-butyl-imino))-erythromycin A Using the procedure of Example 1, 11,12-dideoxy-3-de[(2,6-dideoxy-3-C-methyl-3-0-methyl-α-L-ribohexopyranosyl)-oxy]-6-0-methyl-3-oxo-12, 11-(oxycarbonyl-((4-(4-(3-pyridinyl)-1H-imidazol-1-yl)-butyl-imino))-erythromycin was reacted to obtain the desired product.

EXAMPLE OF PHARMACEUTICAL COMPOSITION

Tablets were prepared containing 150 mg of the product of Example 1 and sufficient excipient of starch, talc and magnesium stearate for a 1 g weight.

PHARMACOLOGICAL STUDY OF THE PRODUCTS OF THE INVENTION

Method of dilutions in liquid medium

A series of tubes was prepared into which an equal quantity of sterile nutritive medium was distributed. Increasing quantities of the product to be studied were distributed into each tube and then each tube was seeded with a bacterial strain. After incubation for twenty-four hours in an oven at 37° C., the growth inhibition was evaluated by transillumination which allowed the minimal inhibitory concentrations (M.I.C.), expressed in micrograms/cm$^3$, to be determined. The following results were obtained:

| GRAM+ Bacterial strains | |
|---|---|
| Products | Ex. 1 |
| Staphylococcus aureus 011UC4 | 0,04 |
| Staphylococcus aureus 011G025I | 0,08 |
| Staphylococcus epidermidis 012GO11I | 0,15 |
| Streptococcus pyogenes group A 02A1UC1 | ≦0,02 |
| Streptococcus agalactiae group B 02B1HT1 | ≦0,02 |
| Streptococcus faecalis group D 02D2UC1 | 0,02 |
| Streptococcus faecium group D 02D3HT1 | ≦0,02 |
| Streptococcus sp group G 02G0GR5 | 0,02 |
| Streptococcus mitis 02mitCB1 | ≦0,02 |
| Streptococcus mitis 02mitGR16I | ≦0,02 |
| Streptococcus agalactiae group B 02B1SJ1 | 0,08 |
| Streptococcus pneumoniae 030SJ5 | 0,02 |

Moreover, the product of Example 1 showed a very useful activity on the following gram (−) bacterial strains: Haemophilus Influenzae 351HT3, 351CB12, 351CA1 and 351GR6.

Various modifications of the products and method of the invention may be made without departing from the spirit or scope thereof and it is to be understood that the invention is intended to be limited only as defined in the appended claims.

What we claim is:

1. A compound selected from the group consisting of a compound of the formula

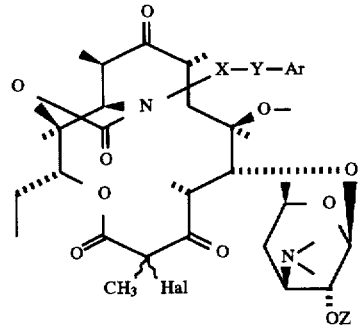

wherein X is selected from the group consisting of —(NH)$_a$—, —CH$_2$—, —SO$_2$— and —O—, a is 0 or 1, Y is selected from the group consisting of —(CH$_2$)$_3$—, —(CH$_2$)$_4$— and —(CH$_2$)-5- Ar is heterocyclic selected from the group consisting of thienyl, furyl, pyrrolyl, thiazolyl, oxazoyl, imidazolyl, thiadiazolyl, pyrazolyl, isopyrazolyl, pyridyl, pyrimidyl, pyridazinyl, pyrazinyl indolyl, benzofuranyl, benzothiazyl and quinolyl or aryl optionally substituted with at least one member of the group consisting of —OH, chlorine, —NO$_2$, —ON,

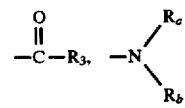

and alkyl, alkyl, alkenyl, alkynyl, alkoxy, alkenyloxy, alkynyloxy, alkythio, alkenylthio, alkynylthio, -N-alkyl, -N-alkenyl and N-alkynyl of up to 12 carbon atoms, R$_a$ and R$_b$ individually are hydrogen or alkyl of up to 12 carbon atoms, R$_3$ is selected from the group consisting of alkyl of 1 to 12 carbon atoms, carbocyclic aryl, carbocyclic aryloxy, carbocyclic arylthio and heterocyclic aryl, heterocyclic aryloxy and heterocyclic arylthio of 5 to 6 ring members containing at least one hetero atom, selected from the group consisting of oxygen, sulfur and nitrogen, Hal is halogen, Z is hydrogen or acyl of an organic carboxylic acid and their non-toxic, pharmaceutically acceptable addition salts.

2. A compound of claim 1 wherein Z is hydrogen.
3. A compound of claim 1 wherein X is —(NH)$_a$— and a is 0 or 1.
4. A compound of claim 1 wherein Hal is fluorine.
5. A compound of claim 1 wherein Ar is heterocyclic aryl.
6. A compound of claim 1 wherein Ar is

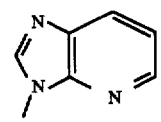

7. A compound of claim 1 wherein Ar is 4-quinolinyl optionally at least mono substituted on one or both quinolinyl rings.
8. A compound of claim 1 wherein Ar is unsubstituted 4-quinolinyl.
9. A compound of claim 1 which is 11,12-dideoxy-3-de[(2,6-dideoxy-3-C-methyl-3-0-methyl-α-L-ribohexopyranosyl)-oxy]-2-fluoro-6-0-methyl-3-oxo-12, 11-(oxycarbonyl((4-(3H-imidazo(4,5-b)-pyridin-3-yl)-butyl)-imino))-erythromycin A.
10. An antibacterial composition comprising an antibactericidally effective amount of a compound of claim 1 and an inert pharmaceutical carrier.

11. A method of treating bacterial infections in warm-blooded animals comprising administering to warm-blooded animals an antibactericidally effective amount of a compound of claim 1.

12. The method of claim 11 wherein Z is hydrogen.

13. The method of claim 11 wherein X is —(NH)$_a$— and a is 0 or 1.

14. The method of claim 11 wherein Hal is fluorine.

15. The method of claim 11 wherein Y is —(CH$_2$)$_3$— or —(CH$_2$)$_4$— or —(CH$_2$)$_5$—.

16. The method of claim 11 wherein Ar is unsubstituted 4-quinolinyl.

17. The method of claim 11 wherein the compound is 11,12-dideoxy-3-de[(2,6-dideoxy-3-C-methyl-3-0-methyl-α-L-ribohexopyranosyl)-oxy]-2-fluoro-6-0-methyl-3-oxo-12, 11-(oxycarbonyl((4-(3H-imidazo(4,5-b)-pyridin-3-yl)-butyl)-imino))-erythromycin A.

* * * * *